June 4, 1974 P. MORDIGAN Plant Pat. 3,565
JUNIPER PLANT
Filed March 26, 1973
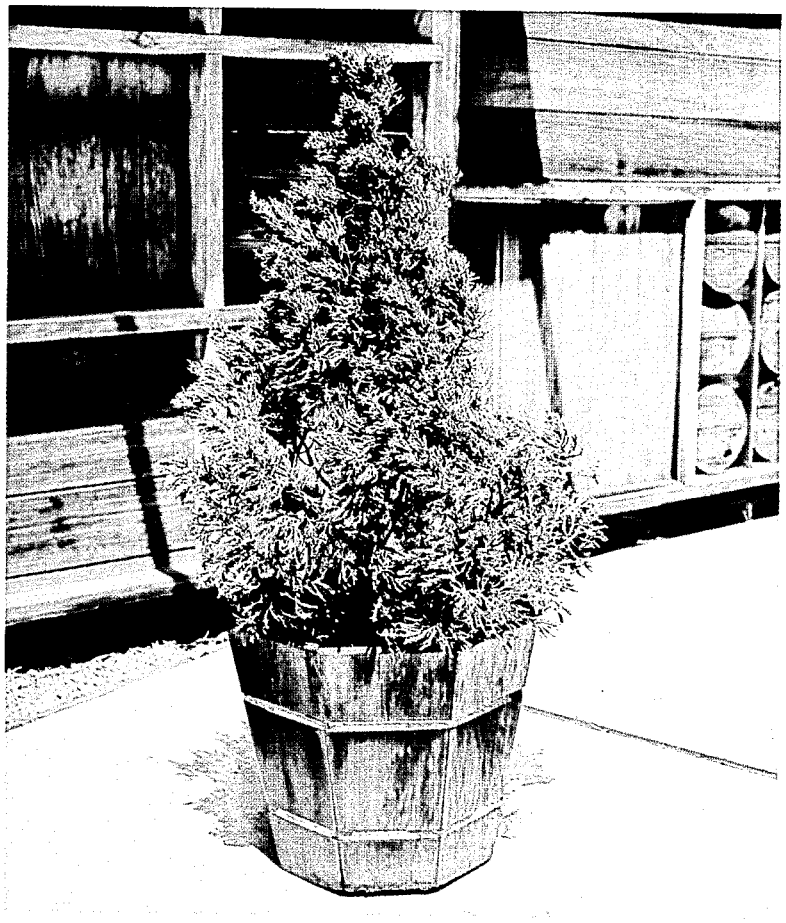

United States Patent Office

Plant Pat. 3,565
Patented June 4, 1974

3,565
JUNIPER PLANT

Peter Mordigan, Sylmar, Calif., assignor to
Select Nurseries, Inc., Brea, Calif.

Filed Mar. 26, 1973, Ser. No. 344,497
Int. Cl. A01h 7/00
U.S. Cl. Plt.—50 1 Claim The present discovery relates to a new and distinct variety of ornamental plant of the Cupressaceae family and more specifically to a plant of the Juniperus genus.

The new and distinct variety was discovered by me as a sport growing from a bed of *Juniperus chinenis* "Torulosa," also known as the Hollywood Juniper, an unpatented variety, in 1954, on my property located at 12851 San Fernando Road, Sylmar, Calif.

Its growth habit differs from the parent plant in that the new variety is a low, upright, compact dwarf evergreen shrub that at maturity attains a height of about four feet and has a spread of from three to four feet, whereas the parent plant has usually attained a height of fifteen feet plus with a spread of about eight to ten feet. At the time the sport was discovered by me the parent plant had already attained a height of between seven and eight feet. The parent plant tends to grow more on a single trunk while the new variety exhibits a prominent central branch that is considerably more branched at the base.

The present variety has been asexually reproduced by me by means of cuttings. The rooted cuttings grow into plants that could be ready for marketing in a relatively time, but due to the fact the plant is a dwarf and is relatively slow growing, it would require considerable time before these plants derived from cuttings would be of any appreciable size.

Asexual reproduction of the new and distinct variety has produced descendants that exhibit the above-described characteristics which shows that the descendants are true and that the new variey has become well established. The plant cannot be reproduced true from seed, in fact up to the present time the new variety has not been observed to produce any seed.

The accompanying drawings in full color show a view of a plant of the new and distinct variety. The new variety retains its pleasant coloration throughout the year and due to its small size and rather slow growth, the plant is ideal for tub use or it may be planted in small containers. The new variety is ideally suited wherever a compact upright evergreen plant is required.

The following is a detailed description of the new and distinct variety. To assist in the identification of the important colors, the nomenclature adopted by the Royal Horticultural Society Colour Charts has been followed.

THE PLANT

General characteristics: The plant is a low, upright, compact, dwarf evergreen shrub that is best described as broadly conical with the top somewhat pointed.

Locality where grown and observed: Sylmar, Calif.

Branches: The plant is much-branched at the base. All branches tend to extend upwardly. The plant has a central trunk or leader.

Colors.—The branches are a reddish-brown in color.

Branches: The plant is much-branched at the base. All which are slender and ascending.

Foliage: Leaves are of two types:

*Juvenile.*—These leaves are at first scale-like and are tightly oppressed, are from 1/16 to 1/8 of an inch in length. These leaves are best described as blunt, they later have a tendency to spread becoming spinecent on the underside. Color: Lettuce Green 861/3.

*Adult.*—Shape: Needle-shaped, stiff, spine tipped. Size and arrangement: Leaves are up to 1/4 inch in length, 2 ranked and alternately arranged. Color: Paris Green 58. Texture: Resinous.

Fruit: The plant is without fruit.

Cones: No cones have been observed.

Seed: The plant has not borne seed to the present time.

I claim:

1. A new and distinct variety of juniper plant substantially as shown and described, characterized by its dwarf size, its slow hardy upright growth habit, its many upwardly extending branches forming a tightly compact bush that is broadly conical having a pointed tip, its resinous foilage that is tightly appressed at first having a tendency to spread somewhat as the leaves mature with said leaves becoming spinescent on the underside, and by the absence of cones and seed.

No references cited.

ROBERT E. BAGWILL, Primary Examiner